(12) United States Patent
Karmarkar

(10) Patent No.: US 8,108,028 B2
(45) Date of Patent: Jan. 31, 2012

(54) MRI SYSTEMS HAVING MRI COMPATIBLE UNIVERSAL DELIVERY CANNULAS WITH COOPERATING MRI ANTENNA PROBES AND RELATED SYSTEMS AND METHODS

(75) Inventor: Parag V. Karmarkar, Columbia, MD (US)

(73) Assignee: Surgi-Vision Inc., Marietta, GA (US)

( * ) Notice: Subject to any disclaimer, the term of this patent is extended or adjusted under 35 U.S.C. 154(b) by 1306 days.

(21) Appl. No.: 11/572,629

(22) PCT Filed: Jul. 26, 2005

(86) PCT No.: PCT/US2005/026508
§ 371 (c)(1),
(2), (4) Date: Jan. 24, 2007

(87) PCT Pub. No.: WO2006/014966
PCT Pub. Date: Feb. 9, 2006

(65) Prior Publication Data
US 2008/0097193 A1 Apr. 24, 2008

Related U.S. Application Data

(60) Provisional application No. 60/591,409, filed on Jul. 27, 2004, provisional application No. 60/608,232, filed on Sep. 9, 2004.

(51) Int. Cl.
*A61B 5/055* (2006.01)
(52) U.S. Cl. ........ 600/423; 600/407; 600/410; 600/411; 600/424; 324/311; 324/322

(58) Field of Classification Search .................. 600/407, 600/410, 411, 423, 424; 604/20, 503
See application file for complete search history.

(56) References Cited

U.S. PATENT DOCUMENTS

| | | | |
|---|---|---|---|
| 5,928,145 | A | 7/1999 | Ocali et al. |
| 6,765,779 | B2 | 7/2004 | Stevenson et al. |
| 6,765,780 | B2 | 7/2004 | Brendel |
| 6,888,715 | B2 | 5/2005 | Stevenson et al. |
| 6,987,660 | B2 | 1/2006 | Stevenson et al. |
| 7,012,192 | B2 | 3/2006 | Stevenson et al. |
| 7,035,077 | B2 | 4/2006 | Brendel |
| 7,038,900 | B2 | 5/2006 | Stevenson et al. |
| 7,136,273 | B2 | 11/2006 | Stevenson et al. |
| 7,310,216 | B2 | 12/2007 | Stevenson et al. |
| 7,489,495 | B2 | 2/2009 | Stevenson |
| 7,535,693 | B2 | 5/2009 | Stevenson et al. |
| 7,623,335 | B2 | 11/2009 | Stevenson et al. |
| 7,689,288 | B2 | 3/2010 | Stevenson et al. |
| 7,751,903 | B2 | 7/2010 | Stevenson et al. |

(Continued)

FOREIGN PATENT DOCUMENTS

EP 1048317 11/2000

(Continued)

*Primary Examiner* — Tse Chen
*Assistant Examiner* — Vani Gupta
(74) *Attorney, Agent, or Firm* — Frommer Lawrence & Haug LLP; Bruce E. Black

(57) ABSTRACT

In vivio deep brain medical probe systems include: (a) an NMRI compatible cannula comprising a plurality of concentric axially extending tubes with a receiving bore; and (b) an elongate antenna member with a conductor and an insulating layer configured to slidably advance through cannula bore to define an MRI receive antenna.

27 Claims, 10 Drawing Sheets

U.S. PATENT DOCUMENTS

| | | |
|---|---|---|
| 7,765,005 B2 | 7/2010 | Stevenson |
| 7,787,958 B2 | 8/2010 | Stevenson |
| 7,822,460 B2 | 10/2010 | Halperin et al. |
| 7,844,319 B2 | 11/2010 | Susil et al. |
| 7,853,325 B2 | 12/2010 | Dabney et al. |
| 7,899,551 B2 | 3/2011 | Westlund et al. |
| 7,916,013 B2 | 3/2011 | Stevenson |
| 7,917,219 B2 | 3/2011 | Stevenson et al. |
| 2001/0053885 A1* | 12/2001 | Gielen et al. .................... 604/20 |
| 2002/0045816 A1 | 4/2002 | Atalar et al. |
| 2003/0009207 A1 | 1/2003 | Paspa et al. |
| 2003/0050557 A1* | 3/2003 | Susil et al. .................... 600/424 |
| 2003/0179536 A1 | 9/2003 | Stevenson et al. |
| 2003/0195405 A1 | 10/2003 | Marino et al. |
| 2003/0213604 A1 | 11/2003 | Stevenson et al. |
| 2003/0213605 A1 | 11/2003 | Brendel et al. |
| 2004/0046557 A1 | 3/2004 | Karmarkar et al. |
| 2004/0201947 A1 | 10/2004 | Stevenson et al. |
| 2004/0257747 A1 | 12/2004 | Stevenson et al. |
| 2005/0007718 A1 | 1/2005 | Stevenson et al. |
| 2005/0190527 A1 | 9/2005 | Stevenson et al. |
| 2005/0201039 A1 | 9/2005 | Stevenson et al. |
| 2005/0219787 A1 | 10/2005 | Stevenson et al. |
| 2005/0247475 A1 | 11/2005 | Stevenson et al. |
| 2005/0248907 A1 | 11/2005 | Stevenson et al. |
| 2006/0028784 A1 | 2/2006 | Brendel |
| 2006/0085043 A1 | 4/2006 | Stevenson |
| 2006/0212096 A1 | 9/2006 | Stevenson |
| 2006/0221543 A1 | 10/2006 | Stevenson et al. |
| 2007/0019362 A1 | 1/2007 | Stevenson et al. |
| 2007/0288058 A1 | 12/2007 | Halperin et al. |
| 2008/0049376 A1 | 2/2008 | Stevenson et al. |
| 2008/0065181 A1 | 3/2008 | Stevenson |
| 2008/0116997 A1 | 5/2008 | Dabney et al. |
| 2008/0119919 A1 | 5/2008 | Atalar et al. |
| 2008/0132987 A1 | 6/2008 | Westlund et al. |
| 2008/0269591 A1 | 10/2008 | Halperin et al. |
| 2009/0116167 A1 | 5/2009 | Stevenson et al. |
| 2009/0259265 A1 | 10/2009 | Stevenson et al. |
| 2010/0016936 A1 | 1/2010 | Stevenson et al. |
| 2010/0023000 A1 | 1/2010 | Stevenson et al. |
| 2010/0023095 A1 | 1/2010 | Stevenson et al. |
| 2010/0066371 A1* | 3/2010 | Vij .................... 324/318 |
| 2010/0160997 A1 | 6/2010 | Johnson et al. |
| 2010/0168821 A1 | 7/2010 | Johnson et al. |
| 2010/0174349 A1 | 7/2010 | Stevenson et al. |
| 2010/0191236 A1 | 7/2010 | Johnson et al. |
| 2010/0198312 A1 | 8/2010 | Stevenson et al. |
| 2010/0217262 A1 | 8/2010 | Stevenson et al. |
| 2010/0222857 A1 | 9/2010 | Halperin et al. |
| 2010/0280584 A1 | 11/2010 | Johnson et al. |
| 2010/0321163 A1 | 12/2010 | Stevenson |
| 2010/0324639 A1 | 12/2010 | Stevenson et al. |
| 2010/0329527 A1* | 12/2010 | Iannotti et al. ................. 382/131 |
| 2011/0022140 A1 | 1/2011 | Stevenson et al. |
| 2011/0040343 A1 | 2/2011 | Johnson et al. |
| 2011/0054582 A1 | 3/2011 | Dabney et al. |
| 2011/0210731 A1* | 9/2011 | Walsh .................... 324/307 |

FOREIGN PATENT DOCUMENTS

| | | |
|---|---|---|
| WO | WO-0038574 | 7/2000 |
| WO | WO 2004095281 A2 | 11/2004 |
| WO | WO 2005114685 A1 | 12/2005 |

* cited by examiner

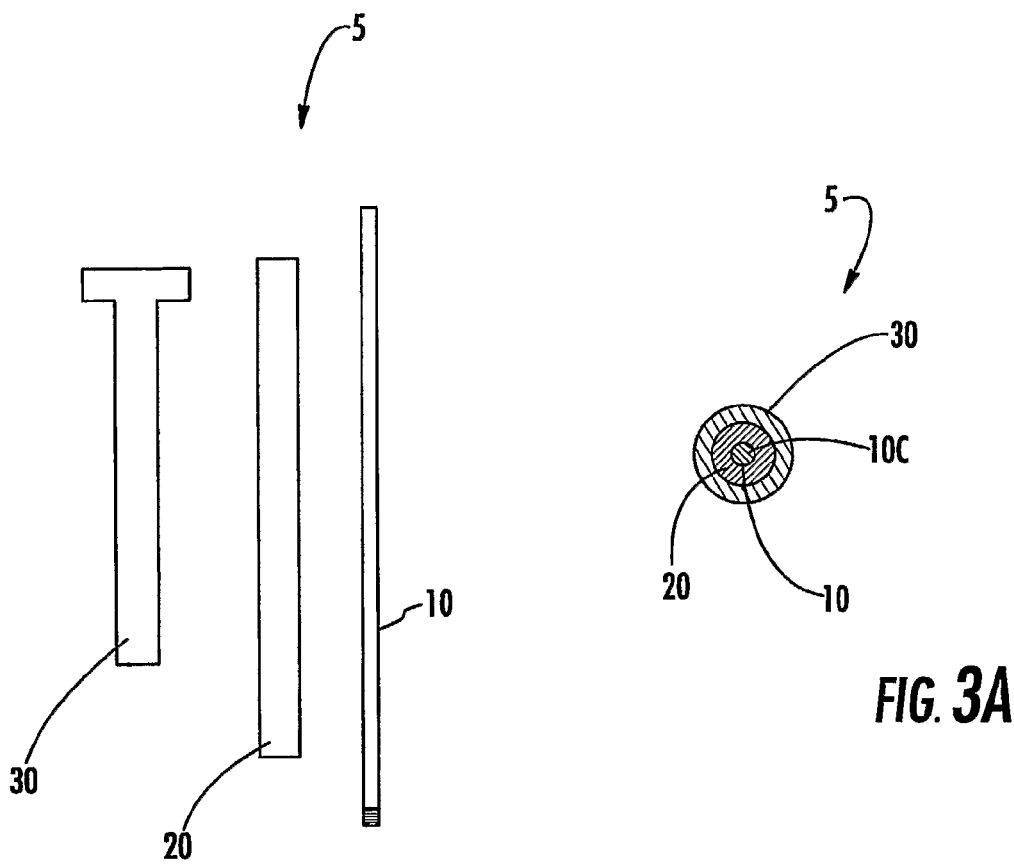
FIG. 2
FIG. 3A
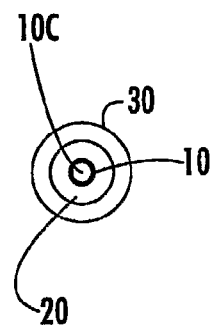
FIG. 3B

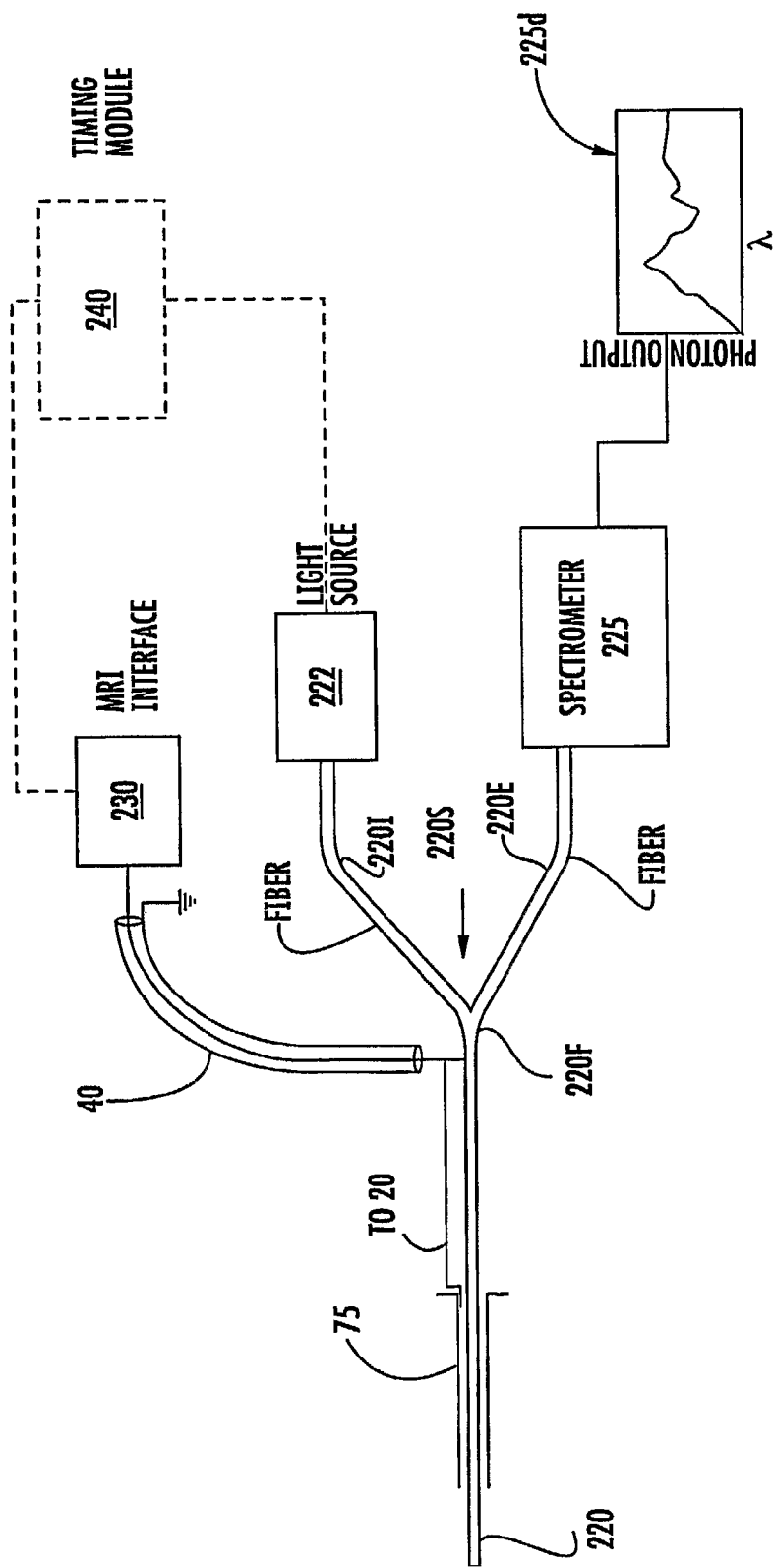

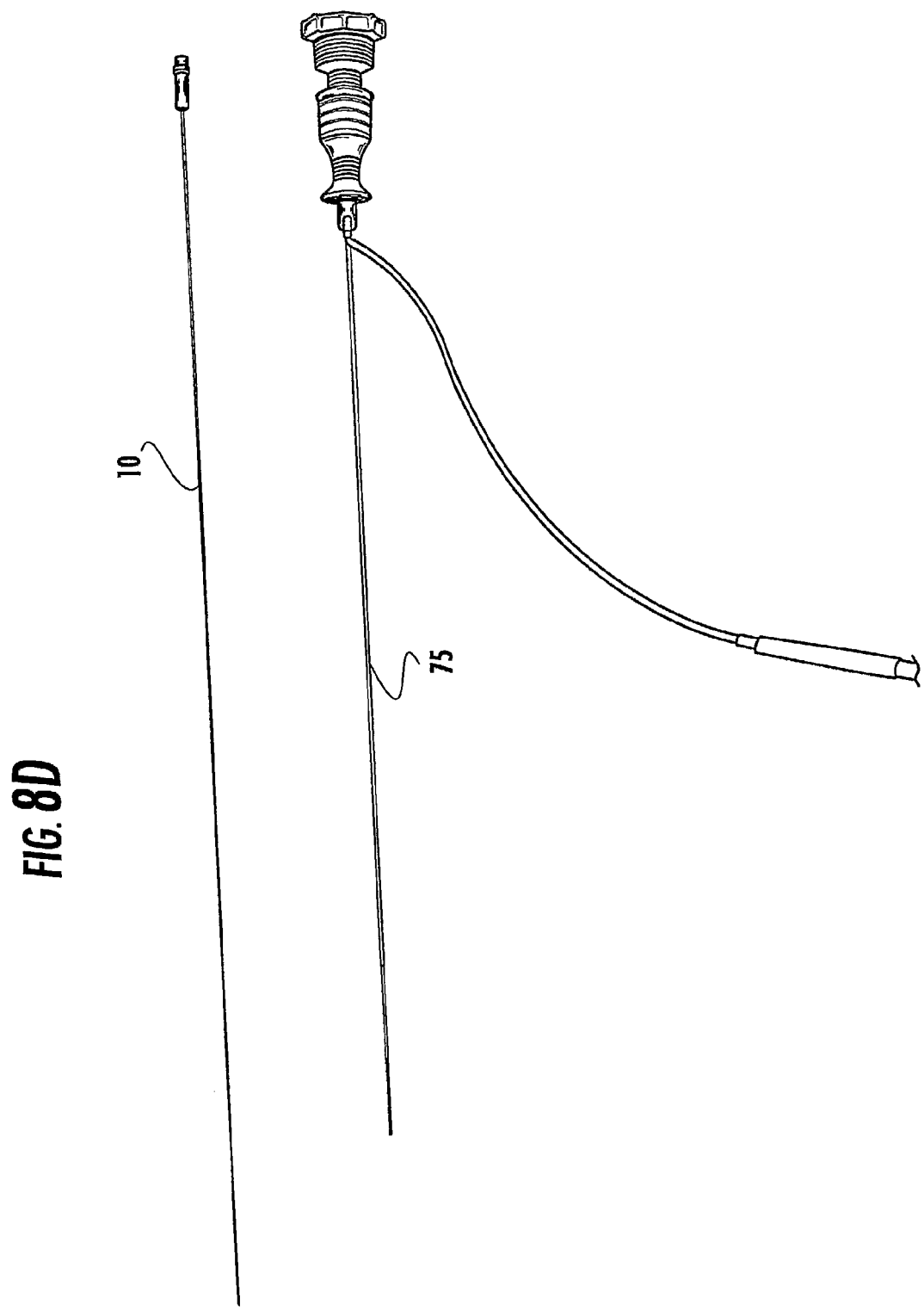

MRI SYSTEMS HAVING MRI COMPATIBLE UNIVERSAL DELIVERY CANNULAS WITH COOPERATING MRI ANTENNA PROBES AND RELATED SYSTEMS AND METHODS

RELATED APPLICATIONS

This application claims the benefit or priority to U.S. Provisional Patent Application Ser. No. 60/591,409, filed Jul. 27, 2004 and U.S. Provisional Patent Application Ser. No. 60/608,232, filed Sep. 9, 2004, the contents of these applications are hereby incorporated by reference as if recited in full herein.

FIELD OF THE INVENTION

The present invention relates to medical leads and may be particularly suitable for use with MRI compatible medical instruments such as implantable Deep Brain Stimulation ("DBS") leads and/or implantable sympathetic nerve chain stimulation leads.

BACKGROUND OF THE INVENTION

Deep Brain Stimulation (DBS) is becoming an acceptable therapeutic modality in neurosurgical treatment of patients suffering from various conditions, including, for example, chronic pain, Parkinson's disease, essential tremor, dystonia and other medical conditions. Other electro-stimulation therapies have also been carried out or proposed using internal stimulation of the sympathetic nerve chain and/or spinal cord, etc.

One example of a prior art DBS system is the Activa® system from Medtronic, Inc. The Activa® system includes an implantable pulse generator stimulator that is positioned in the chest cavity of the patient and a lead with axially spaced apart electrodes that is implanted with the electrodes disposed in neural tissue. The lead is tunneled subsurface from the brain to the chest cavity connecting the electrodes with the pulse generator. These leads can have multiple exposed electrodes at the distal end that are connected to conductors which run along the length of the lead and connect to the pulse generator placed in the chest cavity.

Generally described, electrostimulation is carried out by delivering a pulse of desired frequency and amplitude in the target cranial tissue, typically using an implanted lead system. These lead systems have electrodes that are exposed at a distal end to contact the target cranial/neuronal tissue. The lead systems are connected to an implanted pulse generator at the other opposing end (proximal end). The distal end of the lead system is implanted in the desired cranial anatomy by stereotactic surgical procedures. In this procedure, a microelectrode system is advanced in the cranial tissue, typically based on MRI, CT or PET images acquired prior to the procedure. The target location for lead implantation in the cranial anatomy may be determined by measuring the electrical signal (EPG) signature of the specific anatomy using a microelectrode system. Typically these procedures are long and there is a clinical need for real time imaging guidance.

Notwithstanding the above, there remains a need for alternative MRI compatible medical lead configurations.

SUMMARY OF EMBODIMENTS OF THE INVENTION

Embodiments of the present invention provide MRI compatible imaging systems comprising an MRI compatible cannula and a cooperating microelectrode system that provide an internal MRI antenna. Certain embodiments are particularly suitable for identifying deep brain target locations for implanting stimulation devices. The systems may be used to access various parts of the cranial tissue using substantially real-time MRI for guiding an implantation and/or interventional procedure. These devices can obtain MRI signals environment to obtain MRI images of the local surrounding anatomy and may be used to detect and/or measure the electrical pulses of the cranial tissue.

Certain embodiments are directed to in vivo deep brain medical probe systems include: (a) an MRI compatible cannula comprising a plurality of concentric axially extending tubes with a receiving bore; and (b) an elongate antenna member with a conductor (which may be a center conductor) and an insulating layer configured to slidably advance through cannula bore to define an MRI receive antenna.

Other embodiments are directed to MRI compatible deep brain imaging and recording probe systems that include: (a) a flexible elongate inner member body having opposing proximal and distal portions, the inner member body comprising at least one recording electrode disposed on the distal portion, the inner member comprising at least one axially extending conductor disposed in a core of the inner member body and an axially extending insulating layer surrounding the conductor for at least a major portion of the length of the conductor; (b) a cannula member having increased rididity relative to the inner member and sized and configured to slidably receive the flexible inner member therethrough, wherein, the inner member and cannula cooperate to define an MRI antenna; (c) an RP transmit decoupling circuit in communication with the inner member with the decoupler circuit configured to decouple the MRI antenna during an MRI RF excitation transmission; and (d) a splitter circuit in communication with the inner member to electrically isolate a recording circuit from an MRI imaging circuit.

Other embodiments are directed a medical kit include: (a) an elongate sterilized bio and MRI compatible internal MRI-antenna probe member having opposing distal and proximal portions, the probe comprising a core with a center conductor and at least one recording electrode in communication with the conductor on the distal portion; and (b) a generally rigid cannula comprising at least two concentric tubular members sized and configured to slidably receive the elongate MRI antenna probe therein. In operation, the MRI antenna probe lead cooperates with the cannula to define an internal MRI antenna.

The kit can also include an implantable flexible elongate stimulation probe sized and configured to slidably extend through an axially extending bore of the cannula.

Still other embodiments are directed to MRI antenna and recording electrode probe systems that include: (a) an MRI compatible cannula having an axially extending bore; (b) an elongate flexible probe having at least one recording electrode held by a distal portion of the probe; and (c) an elongate MRI antenna probe. The probe is configured to slidably extend through the cannula bore, and, in operation, the cannula and antenna probe cooperate to define components of at least one deep brain MRI receive antenna.

Other embodiments are directed to computer program products for operating a multi-purpose MRI compatible recording probe with MRI antenna. The computer program product includes a computer readable storage medium having computer readable program code embodied in the medium. The computer-readable program code includes computer readable program code that controllably engages a first or second operational mode for a MRI compatible recording probe with at least one recording electrode and an MRI antenna. The first operational mode having a first transmission path connecting the MRI antenna with an MRI scanner and decoupling the electrode during MRI operation and the second operational mode having a second transmission path connecting the electrode with a recording source during electrical stimulation or recording.

The computer readable program code may be configured to time the selection of the operational mode to occur proximate in time but after an MRI signal acquisition by the MRI antenna in the first operational mode. The computer readable program code may be configured to obtain microrecordings of local tissue in substantially real time proximate in time to an MRI signal acquisition by the MRI antenna in the first operational mode. The computer readable program code may be configured to obtain a plurality of MRI signals of local neural tissue proximate the MRI antenna in substantially real time, then obtain a plurality of microrecordings of the local neural tissue to allow a clinician to track placement of the probe using both MRI data and audio data.

In some embodiments, the cannula is configured to cooperate with the MRI antenna probe to define an MRI receive antenna when the MRI antenna probe is held inside the cannula. In particular embodiments, the cannula comprises a conductive shielding layer that cooperates with the MRI antenna probe to define an MRI receive antenna during positioning in a body used to obtain MRI signals for MRI positional guidance. In operation, the antenna probe can remain in placed and guide the stimulation probe into position or be removed from the cannula and replaced with the stimulation probe, which is then inserted to the same target location identified by the antenna probe.

Other embodiments are directed to MRI compatible deep brain imaging and probe systems. The systems include: (a) a flexible elongate inner member having opposing proximal and distal portions, the inner member comprising at least one optic fiber in a core of the inner member; (b) a cannula member having increased rigidity relative to the inner member and sized and configured to slidably receive the flexible inner member therethrough, wherein, the inner member and cannula cooperate to define an MRI antenna; and (c) an RF transmit decoupling circuit in communication with the inner member, wherein the decoupler circuit is configured to decouple the MRI antenna during an MRI RF excitation transmission.

These and other embodiments will be described further below.

BRIEF DESCRIPTION OF THE DRAWINGS

FIG. 2 is an exploded schematic view of certain components of the assembly shown in FIG. 1.

FIG. 3A is a sectional view of the device shown in FIG. 2, with the three components assembled together according to embodiments of the present invention.

FIG. 3B is an alternate sectional view of the device shown in FIG. 2, with a hollow core, according to embodiments of the present invention.

FIG. 7C is a schematic illustration of a combination NIR optic and MRI antenna tissue imaging and/or tissue data collection system according to embodiments of the present invention.

FIGS. 8A-8D are digital photographs of a cannula and imaging antenna assembly with interface connectors according to embodiments of the present invention.

DETAILED DESCRIPTION OF EMBODIMENTS OF THE INVENTION

Figure 1:
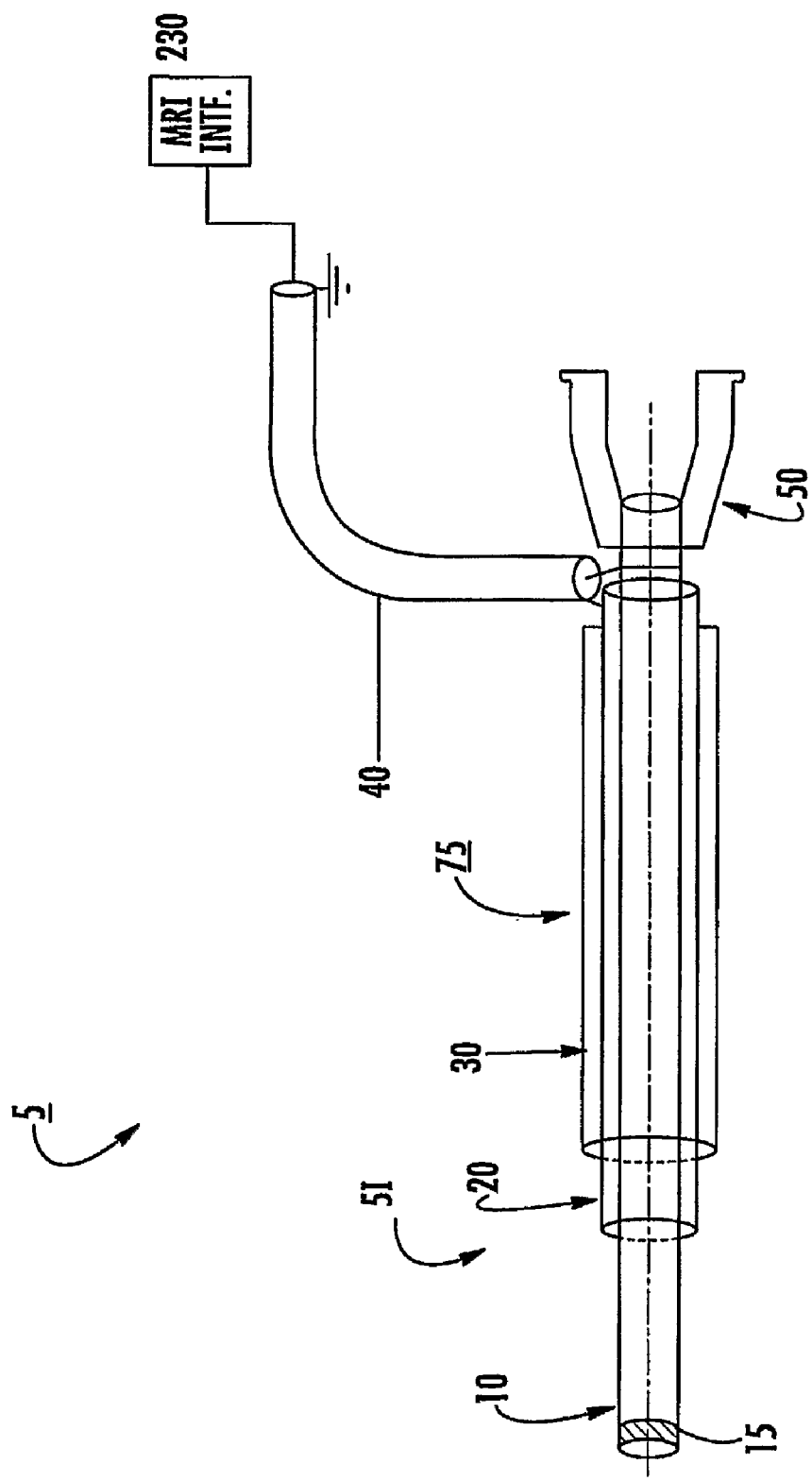
FIG. 1 is a schematic illustration of an MRI assembly with a cannula and elongate internal MRI antenna probe according to embodiments of the present invention.

The present invention will now be described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout. It will be appreciated that although discussed with respect to a certain antenna embodiment, features or operation of one lead system embodiment can apply to others.

In the drawings, the thickness of lines, layers, features, components and/or regions may be exaggerated for clarity and broken lines illustrate optional features or operations, unless specified otherwise. In addition, the sequence of operations (or steps) is not limited to the order presented in the claims unless specifically indicated otherwise. It will be understood that when a feature, such as a layer, region or substrate, is referred to as being "on" another feature or element, it can be directly on the other element or intervening elements may also be present. In contrast, when an element is referred to as being "directly on" another feature or element, there are no intervening elements present. It will also be understood that, when a feature or element is referred to as being "connected" or "coupled" to another feature or element, it can be directly connected to the other element or intervening elements may be present. In contrast, when a feature or element is referred to as being "directly connected" or "directly coupled" to another element, there are no intervening elements present. Although described or shown with respect to one embodiment, the features so described or shown can apply to other embodiments.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and this application and should not be interpreted in an idealized or overly formal sense unless expressly so defined herein.

Probe embodiments of the present invention can be configured to image, record and/or stimulate any desired internal region of the body or object. The object can be any object, and may be particularly suitable for animal and/or human subjects. Some probe embodiments can be sized and configured for deep brain interrogation. Some probe embodiments can be configured to place interventional devices to treat, such as stimulation electrodes to stimulate a desired region of the brain and/or sympathetic nerve chain. Examples of known stimulation treatments and/or target body regions are described in U.S. Pat. Nos. 6,708,064; 6,438,423; 6,356,786; 6,526,318; 6,405,079; 6,167,311; 6539,263; 6,609,030 and 6,050,992, the contents of which are hereby incorporated by reference as if recited in full herein.

FIG. 1 illustrates a first embodiment of an MRI probe assembly 5 that can define an internal MRI antenna 5I according to the present invention. As shown, the assembly 5 comprises a plurality of generally concentric members, shown as three members 10, 20, 30. The outer member 30 and/or intermediate member 20 can be a cannula member 75 (FIGS. 7A, 7B) that is configured to remain in position and guide a stimulation lead 100 or other therapeutic device into the target location using data obtained from the MRI antenna. Additional generally concentric members can be used, such as a fourth outermost member, or even more members. Referring again to FIG. 1, the inner member 10 can include a conductive core which can be hollow or solid. In some embodiments, the core can comprise a relatively thin elongate axially extending insulated lead wire that is insulated over its outer surface along at least a major length of its body. The intermediate member 20 can be insulated from the inner member 10 and may cooperate with the inner member 10 to define a shield for the internal MRI antenna 5I. The outer member 30 can be connected to the intermediate member 20 at a proximal end portion thereof and may also be insulated along its length. The inner member 10 can be configured to slide through the bore of the intermediate 20 and/or outer member 30 to allow for in situ extension beyond the bounds of the intermediate member 20 and/or outer member 30 during a procedure. The intermediate member 20 can be configured to slide through the bore of the outer member 30 or the intermediate member can be affixed to the outer member 30. Each of the members 10, 20, 30 may comprise concentrically configured tubing (such as NITINOL) of increasing size. The outer member 30 can be more rigid than the inner and/or intermediate members 20, 30.

FIG. 2 illustrates an exploded view of one embodiment of the assembly 5. As shown, the inner member 10 can have a first length that is longer than the length of either the intermediate or outer member 20, 30. The intermediate member can have a length that is less than the inner member 10, but longer than the outer member 30. In some particular embodiments, the intermediate member 20 is about 1-3 cm shorter than the inner member 10 and the cannula or outer member 30 can be about 1-4 cm shorter than the intermediate member 20. In some embodiments (such as for deep placement), the overall length of the inner member 10 can be about 10 inches to about 13 inches. The members 10, 20 and 30 can be provided as differently sized sets that allow for deep or shallow placement. The shallow probe placement can employ lengths that are ⅕-⅓ the length of the deep placement members.

FIG. 3A illustrates that the members 10, 20, 30 can be sized and configured to snugly abut each other. In other embodiments, the members 10, 20, 30 may have relatively small radial air gap spaces. Biocompatible anti-friction coatings may be used to facilitate in situ adjustment (extension and/or retraction of the inner member 10) during a procedure. FIG. 3A also illustrates that the inner member core 10c can be solid. FIG. 3B illustrates that the inner member core 10c can be open, allowing for additional interventional probes to be guided/inserted therethrough without removing the inner member 10.

Figure 4:
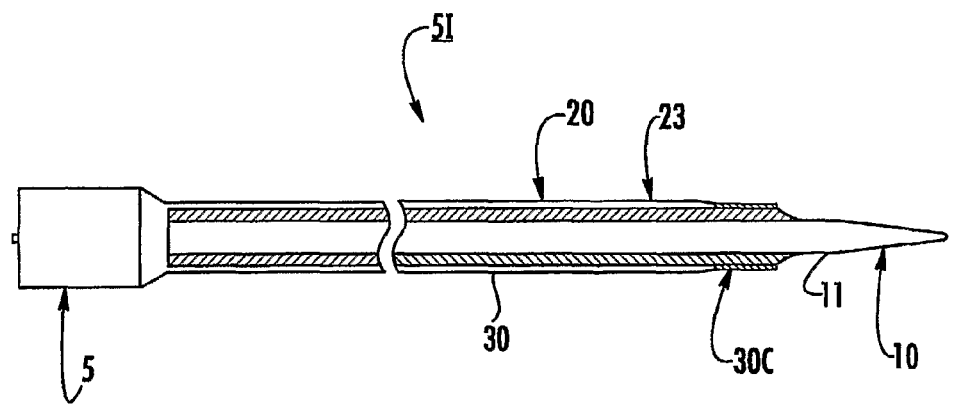
FIG. 4 is a schematic illustration of an internal MRI antenna having a loopless antenna configuration according to embodiments of the present invention.

FIG. 4 illustrates that in some embodiments, the assembly 5 can be configured to define a loopless MRI antenna 5I. The inner member 10 can include a core that is plated with a conductive material or coating for improved conductivity and an outer layer of a thin dielectric 11. The dielectric can terminate to expose the distal end or tip. The outer tubing layer 30 can define a shield. The intermediate member 20 can include a dielectric layer 23 that may be coated for improved conductivity. A distal section of the outer tube 30 can be coiled 30c to improve loading. The proximal portion of the body of the assembly 5 can connect to a micro BNC connector 52, as shown.

FIG. 1 illustrates that a coaxial cable 40 can electrically connect to the inner member 10 and the intermediate member 20. The inner member 10 can merge into a connector 50 at its proximal end portion. The coaxial cable 40 can connect to an MRI scanner interface 230 and the connector 50 can communicate with a recorder (see, e.g., FIG. 5).

In some embodiments, as shown in FIG. 1, the inner member 10 can include at least one recording electrode 15 on a distal portion thereof. For neural uses, different regions in the brain provide different "signature signals" with intensities, frequencies and/or pitches (typically readings of between about 1-4 microvolts) which can be sensed or recorded and are identifiable.

In this embodiment, the conductive core 10c can connect to the electrode 15 and the insulating layer on the inner member 10 can be configured to expose the electrode 15 (i.e., the insulating layer or material can provide a gap or terminate at the location of the electrode). The electrode 15 can be generally cylindrical or configured in any desired configuration. In this embodiment, the assembly 5 can define a bimodal device that provides both a microelectrode recording operational mode as well as an internal MRI antenna receive mode (typically electrically isolated so that each mode is not concurrently operative).

Figure 5:
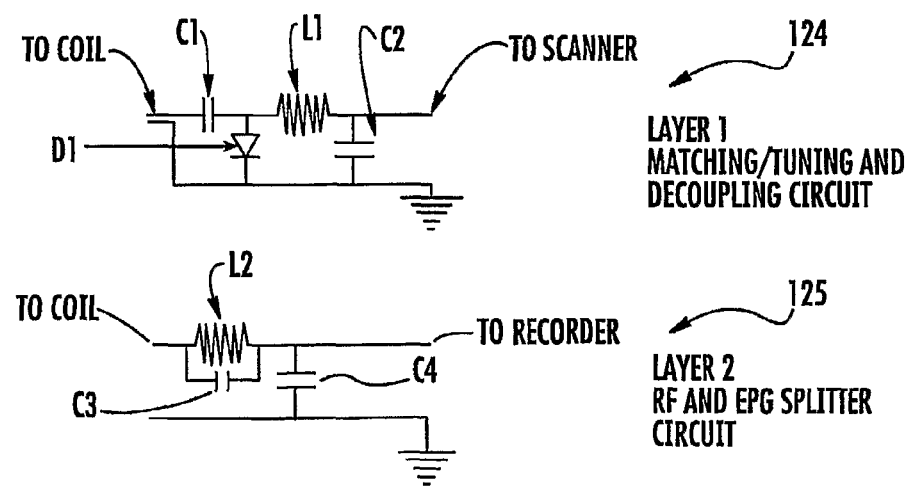
FIG. 5 is a schematic illustration of a matching tuning decoupling circuit and an RF-recording electrode splitter circuit that is operatively associated with an MRI probe assembly according to embodiments of the present invention.

Generally stated, the assembly 5 can be configured so that components of the cannula 75 and microelectrode 15 system form one or more internal MRI RF antennas 5I that can be matched and tuned at the MRI frequency of interest. The assembly 5 can include or be in communication with a matching/tuning and RF decoupling circuit 124 (FIG. 5) as well as a splitter circuit 125 (FIG. 5). The matching/tuning and RF decoupling circuit 124 is configured to decouple the probe during RF excitation so as to inhibit operation during active RF transmission (activating the antenna to receive MRI signals after RF excitation). The splitter circuit 125 can be configured to electrically isolate the probe or separate the operation of the MRI RF signal(s) from the microelectric recording (EPG) signal(s). The splitter circuit 125 can include either a high pass and/or a low pass filter. Additional components of the antennas can be implemented as RF chokes as described for example, in U.S. Pat. No. 6,284,971, the contents of which are hereby incorporated by reference as if recited in fall herein. The term "RF chokes" refers to a shielding layer configuration that provides an electrical length of less than or equal to $\lambda/4$ (from the perspective of external electromagnetic waves) to inhibit the formation and/or propagation of RF induced current or standing waves in an AC (alternating current, e.g., diathermy applications) or RF exposure environment. The physical length that provides the electrical wavelength may vary depending on the materials used in fabricating the probe (such as dielectric constant) and the magnetic field in which it is used.

In some embodiments, a typical system 5 may comprise two discrete members, a cannula 75 and an inner tubular member 10, that may be an insulated wire, that can be termed an MRI antenna probe 10. The cannula 75 can comprise two or more concentric tubes, each insulated from the other and arranged to form an MRI antenna 5I, namely a loopless/dipole antenna (FIG. 4). If two concentric tubes, insulated from each other, are used, the inner tube 10 forms the core of the loopless antenna and the outer tube forms the shield. In case of more than two tubes, e.g., three tubes, the tubes can be arranged so that the innermost tube 10 forms the core, the intermediate 20 the shield/ground and the outermost 30 can be connected to the intermediate tubing at the proximal end to form an RF choke as shown in FIG. 1.

An internal member 10 can cooperate with the cannula 75 and act as an MRI antenna 5I (an RF antenna), which is advanced in the cannula 75 and used to obtain an MRI image of the surrounding anatomy. A recording electrode 15 thereon can be used to obtain and/or measure microelectric signals from the intracranial tissue. The MRI image data and microrecording data can facilitate more exact identification of target cranial anatomy for placement of an implantable DBS lead systems.

As shown in FIG. 5, the shield 30c can be coiled in the distal section to reduce the overall loading length. The entire length of the inner member 10 may be insulated with a polymeric dielectric, except for the distal tip of the inner member 10 and, in some embodiments, the distal tip of the shielding 11. This is to allow measurement of the EPG or EEG signal from the cranial tissue. If the EPG measurement is not a desired feature, the entire length of the inner member 10 may be insulated to prevent contact with biological fluids. At the proximal end of the inner member 10a micro-BNC connector 52 facilitates connecting to a matching/tuning and decoupling circuit and/or a RF-EPG signal splitter circuit, as shown in FIG. 5.

Figure 6:
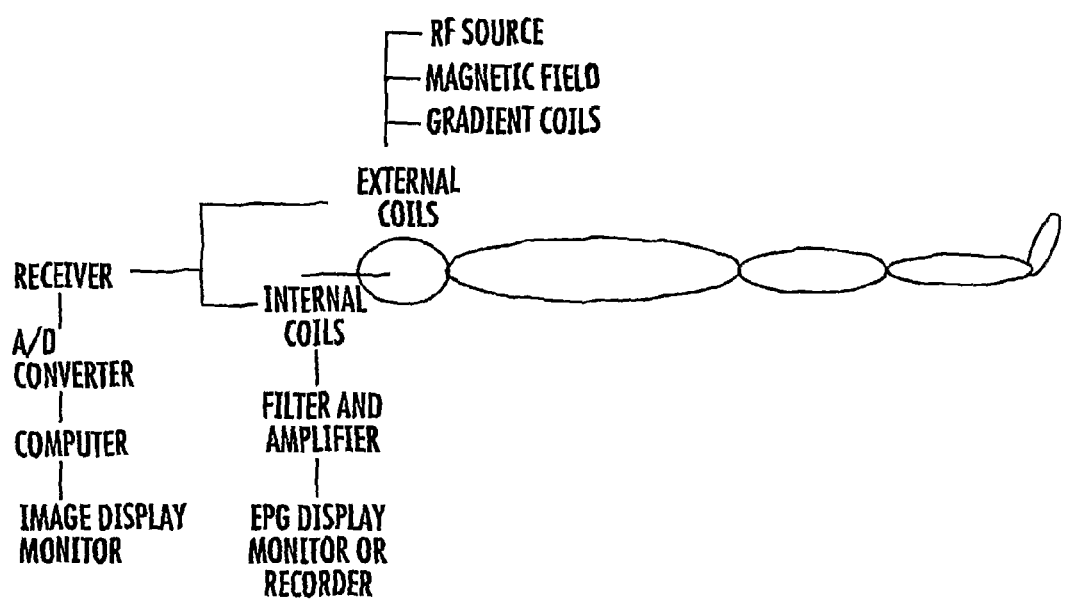
FIG. 6 is a schematic illustration of an MRI probe assembly used for deep brain procedures with an MRI system according to embodiments of the present invention.
Figure 7A:
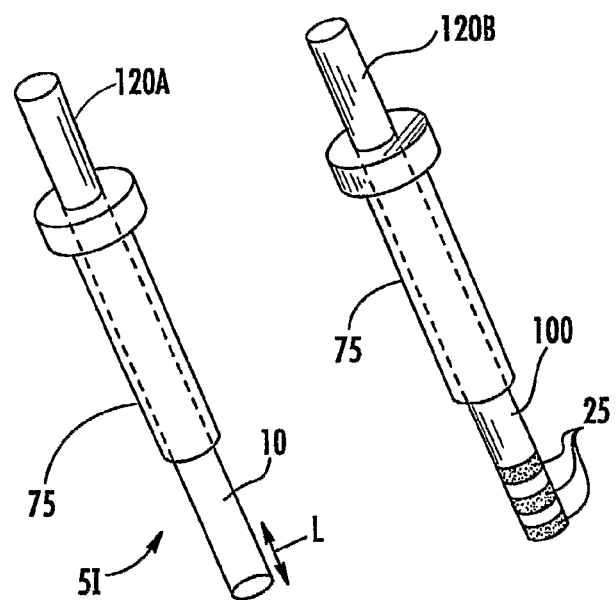
FIG. 7A is a schematic illustration of an MRI probe assembly having a cannula sized to receive both an MRI antenna probe and a stimulation probe according to embodiments of the present invention.

The system 5 may be used with an MRI scanner as shown in FIG. 6. Once the MRI antenna 5I and/or micro-electrode system is used to identify the intracranial location to implant the lead systems, the inner member 10 (and as appropriate, the intermediate tubing 20) can be removed and a lead system or other interventional device can be introduced (and implanted as desired) using the cannula 75 as shown in FIG. 7A. Alternatively, the lead system or other interventional device can be positioned with the inner member 10 in place where the inner member comprises a hollow core as shown in FIG. 3B.

In some embodiments, the inner member 10 and the cannula 75 can be made to work in conjunction with each other, where the function of the cannula tubings can be dependent on the length of the member 10 in the cannula 75. In a typical procedure, the cannula 75 will be advanced in the cranial anatomy, and the imaging coil will be advanced in the cannula and into the tissue. When the antenna probe member 10 is partially outside the distal end of the cannula 75, the probe 10 acts as the core 10c of the loopless antenna 5I and the cannula 75 as the shield of the loopless antenna. When the antenna probe 10 is outside the cannula 75 to a desired length, the cannula 75 ceases to act as the shield but acts as an RF choke to the inner member 10. This mechanism can be built in into the handle section of the inner member 10.

In other embodiments the cannula can be configured to define all or a portion of an inductor loop antenna configuration, a multiple inductor loop configuration, an opposed solenoid coil, etc. The inner imaging antenna probe may be configured in other manners, such as, but not limited to an inductor loop coil, a quadrature loop coil, etc.

It is also noted that the RF splitter circuit 125 (FIG. 5) may be implemented in the ground circuitry, if the distal end of the coiled shield 30c is used to obtain or measure micro recording or EP signals.

In another embodiment, the concentric tubings 20, 30 of the cannula 75 system 5 are not permanently connected to each other and are able to slide inside the other as noted above. Depending on their relative positions, the components perform different electrical functions. For example, the cannula 75 can include two concentric tubings, which slide relative to each other and can be removed as desired or appropriate during the procedure. When the inner tubing 10 extends out of the intermediate tubing 20, it can act as the core of the loopless antenna. The inner member 10 can also include one or two or more concentric (which may be slidable) tubes, all insulated from each other, and with an innermost wire. Thus, when extended or advanced, the innermost wire forms the core of the loopless antenna, and the outer tubings can form the shield and/or the balun. Also the cannula related tubings can form a part of the shield or the RF choke balun, depending on the location of the inner coils with respect to the cannula tubings.

The cannula 75 can be configured with a generally rigid body and/or a body that has increased rigidity relative to at least the inner member 10. The cannula 75 can be configured to slidably receive at least the distal and intermediate portions of the inner member 10 and/or probe body 100 (FIG. 7A) to guide the inner member 10 into position. The cannula 75 and/or associated members 10, 20, 30 can be single-use and disposable and provided as a sterilized component in a medical kit, or it may be re-used as a standard component and sterilized by the user/clinic. The cannula 75 can be configured according to a desired body entry location; e.g., for oral entry, the cannula 75 can be formed into a bite block, nasal cavity or ear plug member, and for non-neural uses, such as placement in the spinal column, no cannula may be required.

For MRI compatible uses, the cannula 75, the members 10, 20, 30, an MRI interface cable and connectors 40, 50 can comprise non-magnetic MRI compatible material(s). In some embodiments, the kit can include an implantable pulse generator 50 as well as the implantable stimulation lead 100 which may also comprise MRI compatible materials to allow post-placement MRI interrogation of the subject. As described above, the stimulation lead 100 can be configured to be guided through the same cannula 75 as the antenna 5I. In some embodiments, the antenna core 10 is removed after a desired location is determined, then the stimulation lead or other device is guided through the cannula 75 to the target location. In other embodiments, the core remains in position and the interventional device guided therethrough as noted above.

The MRI antenna 5I is configured to pick-up MRI signals internally from local tissue during an MRI procedure. In some embodiments, the antenna 5I has a focal length or signal-receiving length of between about 1-5 cm, and typically is configured to have a viewing length to receive MRI signals from local tissue of between about 1-2.5 cm. The MRI antenna 5I can be a loopless antenna such as shown in FIG. 4. However, other antenna configurations can be used, such as, for example, a whip antenna, a coil antenna, and/or a looped antenna. See, e.g., U.S. Pat. Nos. 5,699,801; 5,928,145; 6,263,229; 6,606,513; 6,628,980; 6,284,971; 6,675,033; and 6,701,176, the contents of which are hereby incorporated by reference as if recited in full herein. See also U.S. Patent Application Publication Nos. US 2003/0050557; US 2004/0046557; and 2003/0028095, the contents of which are also hereby incorporated by reference as if recited in full herein. The antenna may be used to guide placement of interventional probes and are not necessarily used to generate images of local structure.

It is contemplated that the electrode(s) of the antenna 5I and/or the stimulation lead 100 can be sized and configured to "fit" the desired internal target, which may be a relatively small region, such as less than about 1-3 mm. Typically, as shown in FIG. 1, the electrode(s) 15 can be held on a distal portion of the probe body.

Generally stated, the assembly has two primary operational modes with different electric transmission paths, which are electrically directed using the splitter circuit 125 (FIG. 5). In operation, during an MRI procedure, an RF excitation pulse is transmitted to a subject. The MRI antenna is decoupled during RF transmission, then operative during a receive cycle to receive signal from local tissue. The recording electrode(s) 15 is typically isolated via the splitter circuit 125 so that only the MRI antenna is active. The MRI interface communicates with the MRI scanner.

During MRI guided clinical implantation of the probe can first be used as an MRI antenna 5I to provide high resolution imaging of the target internal anatomy (such as neural tissue) and to locate the position of the electrode 15 in the body by obtaining MRI signals and hence, images, that are acquired by the external coils and/or internal MRI antenna. The electrodes 15 can also be used to assess location via acquiring or sensing electrical signals from the target (neural) anatomy.

Figure 7B:
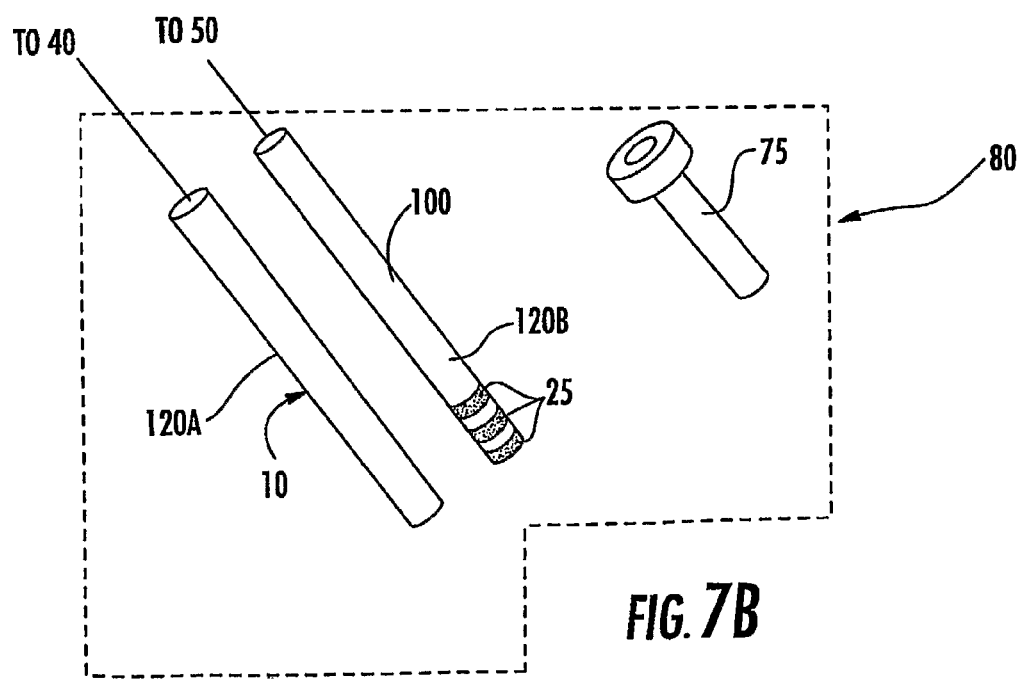
FIG. 7B is a schematic illustration of a medical kit that can provide an MRI compatible cannula and the stimulation and antenna probe shown in FIG. 7A.
Figure 8A:
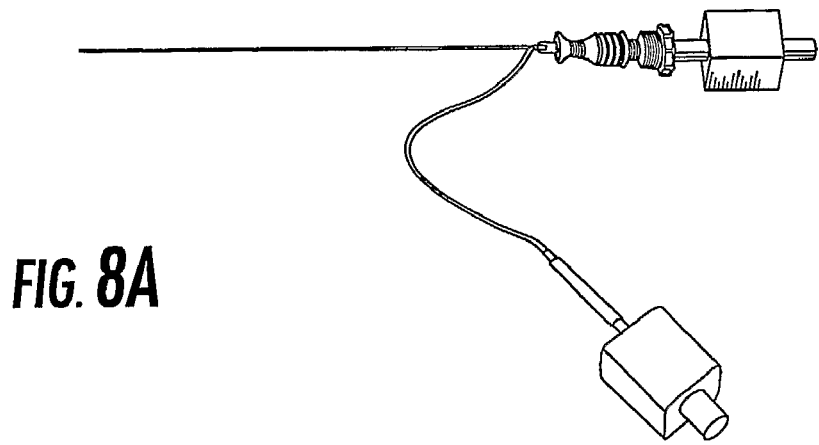
Figure 8B:
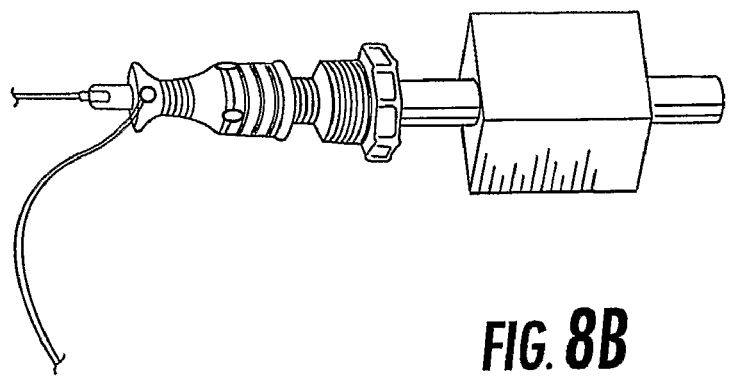
Figure 8C:
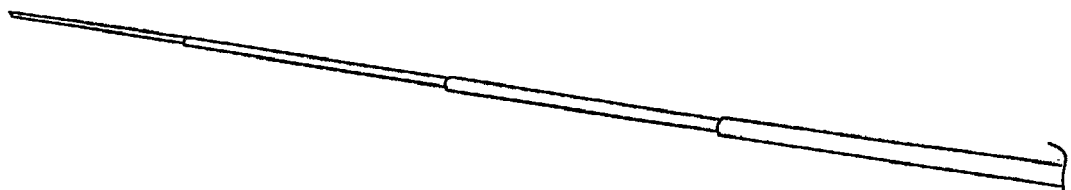

FIGS. 7A and 7B illustrate a dual probe system according to other embodiments of the present invention. In this embodiment, an MRI antenna probe 120a and a stimulation probe 120b can be sized and configured to serially enter a common cannula 75. The antenna probe 120a and/or the stimulation probe 120b can each include at least one sensing electrode. Each probe 120a, 120b can have a graduated scale or coordinate system that allows the antenna probe 120a to be used to obtain MRI imaging data used to locate the target in vivo location. The cannula 75 can include MRI fiducial markers (not shown). The antenna probe 120a can then be removed and replaced with the stimulation probe 120b that can be automatically advanced in the same trajectory to the same position based on the data provided by the antenna probe 120a and the controlled insertion to the location defined by the antenna probe 120a, typically to a high degree of precision. The two probes 120a, 120b can be sized and configured to have substantially the same cross-sectional area. In some embodiments, a non-conductive elastomeric sleeve (not shown), coating or other configuration can be used to size the probes 120a, 120b to snugly fit the cannula 75 as desired. In other embodiments, an insert can be used to adjust the size of the cannula 75 to correspond to that of the probe in use (also not shown).

FIG. 7B illustrates that a kit 80 can comprise the two probes 120a, 120b and, optionally, the cannula 75. The antenna probe 120a can be configured to connect with the MRI interface while the stimulation probe 120b can be configured to connect to the implantable pulse generator, each of which (along with respective leads) may also form part of the medical kit 80.

The cannula 75 may be sized and configured to be a universal delivery system cannula 75 that can slidably serially receive selectable different elongate probes, such as the microelectrode and stimulation electrode probes discussed above. For example, the universal system cannula 75 can be configured to selectably receive different elongate members, such as, but not limited to, at least two of the following MRI compatible devices: an MRI antenna probe, an optic probe, a depth probe, an EEG probe, a stimulation probe (which may be implantable), a biopsy probe, an ablation probe, and a drug and/or fluid delivery and/or extraction probe (catheter, shunt and the like). The MRI antenna probe may be a standalone MRI antenna probe that cooperates with the cannula 75, or may be combined with any of the other probe functions. For example, the probe 5 can be configured to provide a combination biopsy needle and MRI antenna probe when positioned in the cannula 75. An example of a needle antenna is described in U.S. Pat. No. 6,606,513, the contents of which are hereby incorporated by reference as if recited in full herein.

As such, the cannula 75 can have an ID (inner diameter) that allows different selected probes to be guided therethrough, or one or more of the tubes (such as the intermediate tube 20 in a three tube configuration) can be removed when the cannula 75 is used with larger probes. That is, one or more of the cannula tubes can act a removable sleeve for certain probes. In other embodiments, the cannula 75 has a fixed ID, and the different probes have a substantially similar OD (outer diameter), or one or more of the different probes can use sleeves to provide the desired size that allow them to be guided reliably into location with the same cannula 75. The OD of the different selectable inner members, usable with a universal cannula 75, can be between about 0.5-3 mm, and in some embodiments is about 1.5 mm or less, typically about 1.3 mm or less, and more typically between about 1.27-1.3 mm. The OD of the cannula 75 may be about 2 mm. The members 10, 20 and 30 can be provided as differently sized sets that allow for deep or shallow placement. The shallow probe placement can employ lengths that are ⅕-⅓ the length of the deep placement members described above.

The cannula 75 and probe members can be provided as differently sized sets that allow for deep or shallow in vivo placement and/or for use with about a 1.5T or about a 3.0 T MRI System. For brain applications, the shallow probe placement can employ lengths that are at least about 3 cm, typically about 3 cm. The deep placement members can be at least about 7 cm long, typically between about 7-8 cm long. Different French size probes and/or different length probes may generate different loads and tuning may be adjusted accordingly. The antenna probes can be tuned remotely so that substantially the entire length or a selected portion thereof is active.

In some embodiments, as shown in FIG. 7C, the inner member 10 (or one of the selectable inner member probes) can be configured as an NIR (near infrared imaging) optic probe 220. See Giller et al., *Validation of a near-infrared probe for detection of thin intracranial white matter structures*, J. Neurosurg 98: 1299-1306 (2003) and U.S. Pat. No. 6,567,690, the contents of which are hereby incorporated by reference as if recited in full herein. In particular embodiments, the inner member 10 can be configured as a combination NIR optic probe and to provide an MRI antenna as shown in FIG. 7C. For example, the probe 220 can comprise an elongate fiberoptic fiber or fiber bundle 220f that can be cladded (meaning the fiber optic(s) encased) with a desired MRI compatible conductive material, such as gold. The cladding or casing layer may terminate before the distal end of the member 220 (exposing the outer surface(s) of the optic fiber). Placing the cladded fiber optic package in the cannula 75 allows the combination probe 220 to cooperate with the cannula 75 and/or define independently, both an MRI antenna and an NIR imaging device. The probe 220 can be in communication with a light source 222 (typically a broad band light source) and a spectrometer 225 (typically a CCD array spectrometer) via the fiber(s) 220*f*. The spectrometer can provide tissue data 225*d* such as wavelength versus photon output based on local tissue characteristics (i.e., such as reflectance or other desired optical property). The light source 222 and/or the spectrometer 225 can be placed in or out of the MRI suite to avoid MRI interference and/or can be configured with MRI compatible components and materials. As shown, the system can also include an MRI interface 230 electrically connected to the probe 220 via (coaxial) cable 221. The fiber(s) 220*f* can comprise a splitter 220*s* at a proximal end portion to provide separate light input and output paths 220*i*, 220*e*.

The coaxial cable 40 can be in electrical communication with the cladding of the probe 220 as well as the intermediate cannula member 20, as described for the embodiment shown in FIG. 1. Similarly, the MRI antenna or probe can be in communication with an RF decoupler circuit 124 (FIG. 5). An optional light and MRI timer 240 can be used to facilitate concurrent signal acquisition (registration) of a common region. The NIR probe function allows forward views (typically about 1-1.5 mm in front of the probe tip) while the MRI antenna can gather signal data of tissue proximate a distal end portion of the probe.

Figure 9:
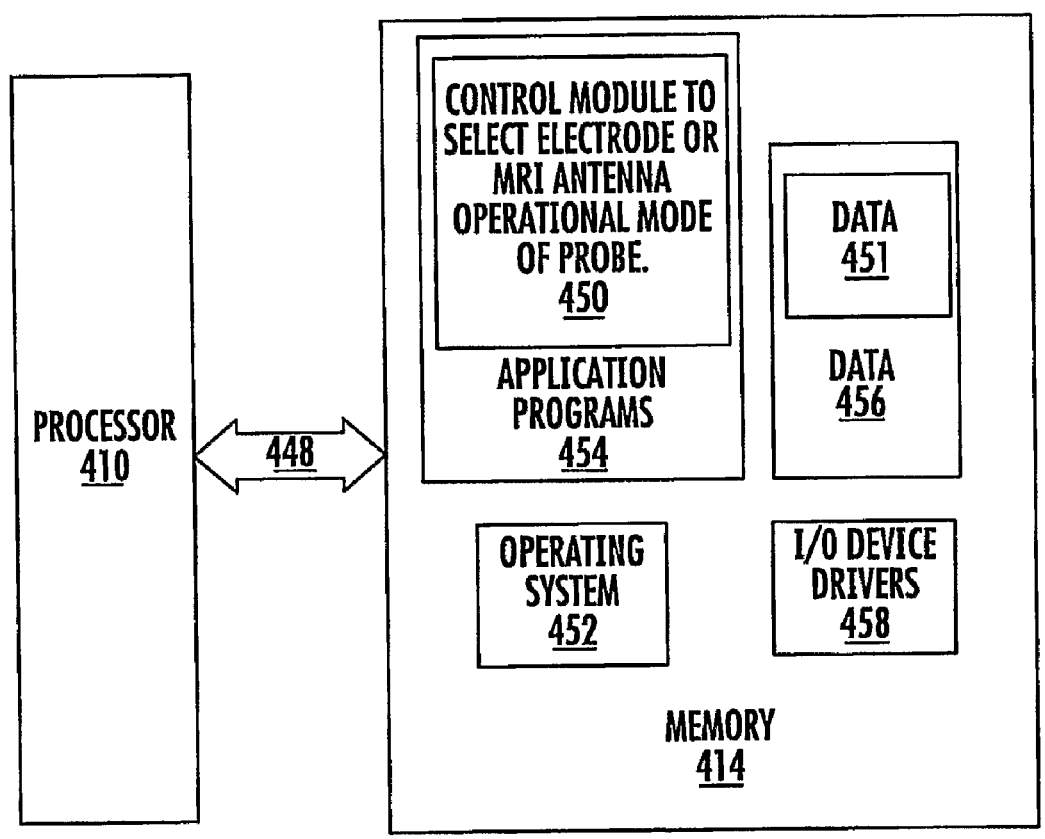
FIG. 9 is a block diagram of a data processing system according to embodiments of the present invention.

FIG. 9 is a block diagram of exemplary embodiments of data processing systems that illustrates systems, methods, and computer program products in accordance with embodiments of the present invention. The data processing systems may be incorporated in a digital signal processor in either the implantable pulse generator and/or MRI scanner interface and/or be in communication therewith. The processor 410 communicates with the memory 414 via an address/data bus 448. The processor 410 can be any commercially available or custom microprocessor. The memory 414 is representative of the overall hierarchy of memory devices containing the software and data used to implement the functionality of the data processing system. The memory 414 can include, but is not limited to, the following types of devices: cache, ROM, PROM, EPROM, EEPROM, flash memory, SRAM, and DRAM.

As shown in FIG. 9, the memory 414 may include several categories of software and data used in the data processing system: the operating system 452; the application programs 454; the input/output (I/O) device drivers 458; the MRI Antenna operation or Electrode Operation Module 450; and data 456.

As will be appreciated by those of skill in the art, the operating system 452 may be any operating system suitable for use with a data processing system, such as OS/2, AIX, DOS, OS/390 or System 390 from International Business Machines Corporation, Armonk, N.Y., Windows CE, Windows NT, Windows95, Windows98, Windows2000 or other Windows versions from Microsoft Corporation, Redmond, WA, Unix or Linux or FreeBSD, Palm OS from Palm, Inc., Mac OS from Apple Computer, LabView, or proprietary operating systems. The I/O device drivers 458 typically include software routines accessed through the operating system 452 by the application programs 454 to communicate with devices such as I/O data port(s), data storage 456 and certain memory 414 components. The application programs 454 are illustrative of the programs that implement the various features of the data processing system and can include at least one application, which supports operations according to embodiments of the present invention. Finally, the data 456 represents the static and dynamic data used by the application programs 454, the operating system 452, the I/O device drivers 458, and other software programs that may reside in the memory 414.

While the present invention is illustrated, for example, with reference to the Module 450 being an application program in FIG. 9, as will be appreciated by those of skill in the art, other configurations may also be utilized while still benefiting from the teachings of the present invention. For example, the Module 450 may also be incorporated into the operating system 452, the I/O device drivers 458 or other such logical division of the data processing system. Thus, the present invention should not be construed as limited to the configuration of FIG. 9 which is intended to encompass any configuration capable of carrying out the operations described herein. Further, the Module 450 can communicate with other components, such as an MRI scanner.

The I/O data port can be used to transfer information between the data processing system or another computer system or a network (e.g., the Internet) or to other devices controlled by the processor. These components may be conventional components such as those used in many conventional data processing systems, which may be configured in accordance with the present invention to operate as described herein.

The computer-readable program code can include computer readable program code that controllably engages a first or second operational mode for a MRI compatible antenna and recording probe with at least one electrode and an MRI antenna. The first operational mode having a first transmission path connecting the MRI antenna with an MRI scanner and decoupling the electrode during MRI operation and the second operational mode having a second transmission path connecting the electrode with a recording source during electrical recording.

The computer readable program code may be configured to time the selection of the operational mode to occur proximate in time but after an MRI signal acquisition in the first operational mode. The computer readable program code may be configured to operate the second mode to obtain microrecordings of local tissue in substantially real time proximate in time to an MRI signal acquisition by the MRI antenna in the first operational mode. The computer readable program code may be configured to obtain a plurality of MRI signals of local neural tissue proximate the MRI antenna in substantially real time, then obtain a plurality of microrecordings of the local neural tissue to allow a clinician to track placement of the probe using both MRI data and audio data.

The flowcharts and block diagrams of certain of the figures herein illustrate the architecture, functionality, and operation of possible implementations of the present invention. In this regard, each block in the flow charts or block diagrams represents a module, segment, or portion of code, which comprises one or more executable instructions for implementing the specified logical function(s). It should also be noted that in some alternative implementations, the functions noted in the blocks may occur out of the order noted in the figures. For example, two blocks shown in succession may in fact be executed substantially concurrently or the blocks may sometimes be executed in the reverse order, depending upon the functionality involved.

The present invention is explained further in the following non-limiting Example.

EXAMPLE 1

Figure 10:
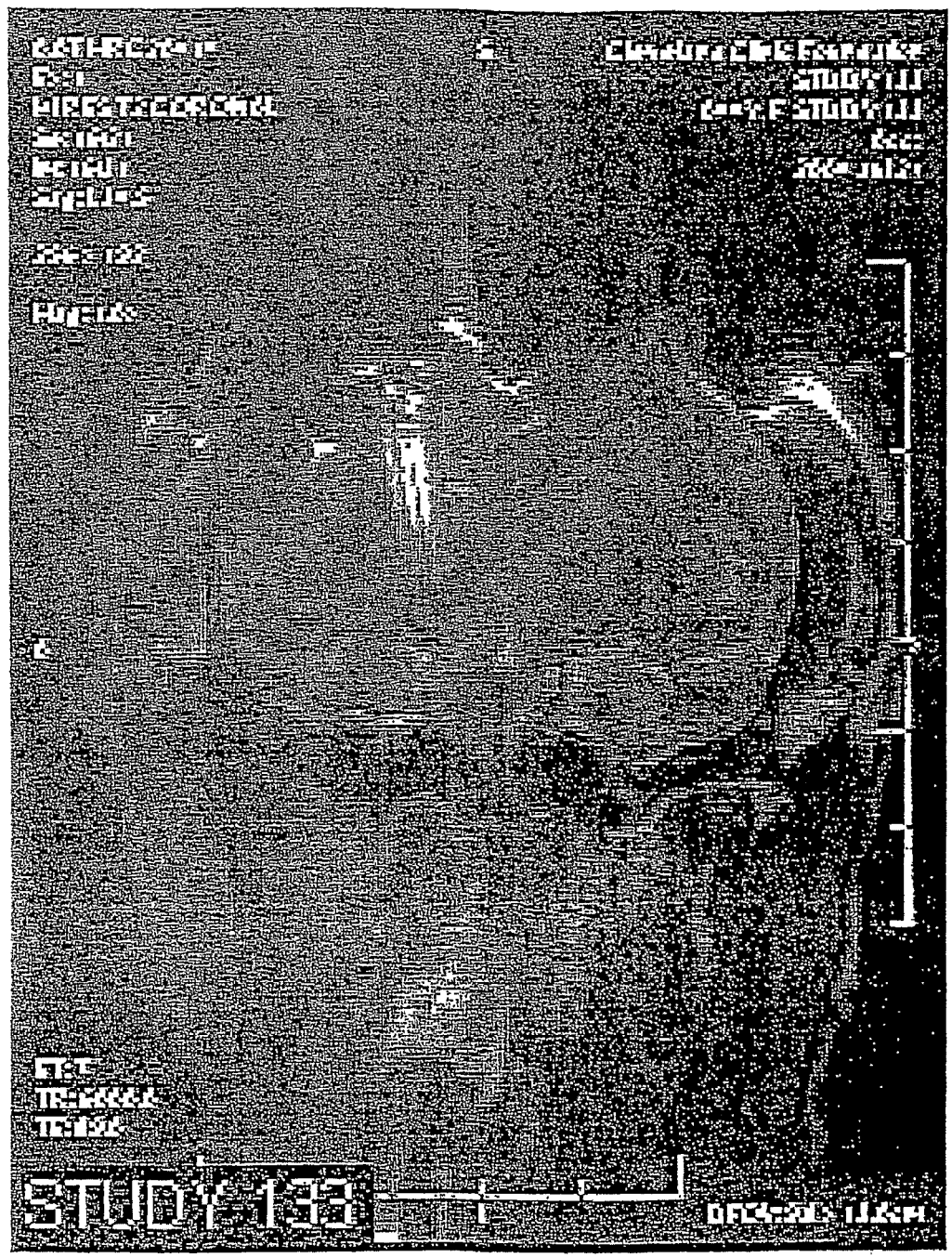
FIG. 10 is a digital image of the device shown in FIGS. 8A-8D in a primate during an investigational study.

FIGS. 8A-8D illustrate a prototype configuration of a cannula 75 with MRI antenna 5I formed by the inner member 10 and cannula 75 that was used to obtain the image of the primate shown in FIG. 10. The MRI compatible cannula and microelectrode configuration was used in vivo with a Siemens Allegra® 2.9T scanner. A 2 mm outer diameter cannula included three concentric insulated tubes from Nitinol configured to define a loopless RF antenna. The innermost tube (1.5 mm inner diameter) formed the core of the loopless antenna and provided a conduit to advance an additional MRI-antenna/microelectrode component. The intermediate tube formed the shield of the antenna with the outermost tube connected to the intermediate tube at a proximal end to form a RF choke. The inner diameter of the cannula and the outer surfaces were coated with a thin polyurethane insulation and the entire cannula part of the assembly was insulated by a 0.001 inch polyimide tube.

The micro-electrode loopless antenna member was fabricated from Nitinol tube with an insulated gold-plated wire inside the Nitinol tube forming the core of the antenna. The dipole end portion of the antenna was about 1.5 cm and was not insulated at the outermost end portion for about 1 mm to permit EEG measurements. The shield of the antenna was coiled at the distal end portion to reduce the overall loading length to about 3 cm. The member was insulated by a 500 micron polyester layer (except for the distal tip of the member to permit EEG measurements as noted above). The cannula and microelectrode antenna member were matched and tuned to about 123.2 MHz and decoupled from pick-up during MRI excitation via a decoupling circuit/switch similar to that described in Ocali et al., *Intravascular magnetic resonance imaging using a loopless catheter antenna*, Magn Reson Med, 1997; 37: pp. 112-118.

MRI testing of the cannula and antenna/microelectrode member were performed on the 2.9T Siemen's Allegra® scanner. RF power deposition safety testing was carried out in a polyacrylamide gel phantom of conductivity 0.9 S/m. A nominal 4W/kg SAR (head) MRI sequence was applied for 3.4 minutes. The cannula and the microelectrode/antenna member were placed about 1 cm from the edge of the phantom and the local temperature was measured directly using FISO fiber-optic temperature probes. Actual SAR was calculated from the rate of the initial temperature rise and the specific heat of the gel. The MRI signal to noise ratio (SNR) of the microelectrode/antenna and cannula system was tested in a saline phantom with variable depths of insertion (3 cm and 10 cm) to simulate some clinical conditions.

The feasibility of using the cannula and microelectrode/antenna system for MRI-guided access to the brain (deep brain), such as the STN (subthalamic nucleus), was tested in a primate with protocols approved by the appropriate Animal Care and Use committee. Preoperative MRI and CT images were obtained to locate a head mount and determined a trajectory for microelectrode advancement. The animal was anesthetized, a burr hole prepared, a head mount assembly fixed to the skull and the cannula/antenna system advanced under real-time MRI guidance to the location of the STN. To increase SNR and field-of-view, images obtained from the scanner's external head coil and the internal antenna probe were combined using a phased array adapter.

The cannula/loopless antenna and coaxial cable had an impedance of about 25 ohms. The RF choke created between the primary and secondary shielding had an isolation of about 550 ohms when the antenna/cannula was loaded up to about 4 cm in the saline phantom. The coaxial cable of the microelectrode/antenna member had an impedance of about 32 ohms. The SNR profile of the antenna demonstrated about a 50% improvement over the external head coil in a circular region of about 5 mm radius around the distal end portion of the antenna/microelectrode member. In the primate study, the signal from the scanner's had coil depicts the overall cranial anatomy while the local SNR enhancement provided by the cooperating MRI compatible cannula and microelectrode/antenna member as the coil advanced into the STN is shown in FIG. 10.

The experiment demonstrated that a cooperating MRI compatible cannula and microelectrode/antenna member suitable for intra-cranial interventions can be fabricated and provide substantial local SNR improvements. The local SNR improvement can provide enhanced local spatial registration for precise anatomical guidance/positioning In the drawings and specification, there have been disclosed embodiments of the invention and, although specific terms are employed, they are used in a generic and descriptive sense only and not for purposes of limitation, the scope of the invention being set forth in the following claims. Thus, the foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses, where used, are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. An in vivo deep brain medical probe system, comprising:
an MRI compatible cannula comprising a plurality of generally concentric axially extending tubes with a receiving bore;
an elongate antenna member with a core comprising a conductor and an insulating layer configured to slidably advance through the cannula bore to cooperate with the cannula to define an MRI receive antenna, wherein the elongate antenna member comprises a center conductor and at least one recording electrode disposed on a distal portion thereof, wherein the probe system has at least two operational modes, including a first MRI signal operational mode wherein the antenna member receives MRI signals from local tissue and a second operational recording signal mode wherein the recording electrode obtains electrical signals from local target tissue;
a tuning circuit coupleable to the MRI receive antenna to tune the MRI receive antenna to a MRI frequency;
a RF decoupling circuit configured to isolate the MRI receive antenna during an MRI excitation RF transmission; and
a recording splitter circuit to decouple the MRI receive antenna during the recording mode.

2. A probe system according to claim 1, further comprising an MRI compatible interventional probe member configured to slidably extend through the MRI compatible cannula, wherein the interventional probe member comprises at least one of an optic probe, an EEG probe, a stimulation probe, a biopsy probe, an ablation probe, a drug delivery probe, a fluid delivery probe, or a fluid extraction probe.

3. A probe system according to claim 1, wherein the antenna member electrically cooperates with the cannula to define a loopless MRI antenna.

4. A probe system according to claim 1, wherein the cannula comprises an intermediate tubular member and an outer member that generally encases at least a major length of the intermediate member.

5. A probe system according to claim 4, wherein the antenna member has a first length, the intermediate member has a second length, and the outer member has a third length, the first length being longer than the second and third lengths, and the second length being longer than the third length.

6. A probe system according to claim 1, in combination with an implantable stimulation lead that is sized and configured to slidably extend through the bore of the cannula after the antenna member is removed therefrom.

7. A probe system according to claim 1, wherein the antenna member comprises a hollow core and is configured to slidably receive selected interventional devices therethrough.

8. An in vivo deep brain medical probe system, comprising:
an MRI compatible cannula comprising a plurality of generally concentric axially extending tubes with a receiving bore;
an elongate antenna member with a core comprising a conductor and an insulating layer configured to slidably advance through the cannula bore to cooperate with the cannula to define an MRI receive antenna; and
a tuning circuit coupleable to the MRI receive antenna to tune the MRI receive antenna to a MRI frequency,
wherein the elongate antenna member comprises a flexible elongate inner member body having opposing proximal and distal portions, the inner member body comprising at least one recording electrode disposed on the distal portion;
the MRI compatible cannula having increased rigidity relative to the elongate antenna member;
the probe system further comprising
an RF transmit decoupling circuit in communication with the elongate antenna member with the decoupler circuit configured to decouple the MRI receive antenna during an MRI RF excitation transmission; and
a splitter circuit in communication with the elongate antenna member to electrically isolate a recording circuit from an MRI imaging circuit.

9. A probe system according to claim 8, wherein the system is configured to attach to an MRI scanner and a recording circuit for selectively operating the recording electrode or the MRI receive antenna.

10. A probe system according to claim 8, wherein the decoupler circuit comprises a matching and tuning decoupling circuit that engages an MRI scanner and decouples the MRI receive antenna during RF transmission.

11. A probe system according to claim 8, wherein the system has selective operative first and second electrical transmission paths associated with first and second operational modes, the first transmission path connecting the MRI receive antenna with an MRI scanner and decoupling the recording electrode during MRI operation and the second transmission path connecting the recording electrode with a recording source during electrical recording, respectively.

12. A probe system according to claim 8, wherein the elongate antenna member has a hollow core.

13. A probe system according to claim 8, wherein the conductor is substantially centrally held in the core.

14. A medical kit, comprising:
(a) an elongate sterilized bio and MRI compatible internal MRI-antenna probe member having opposing distal and proximal portions, the MRI-antenna probe member comprising a core with a conductor and at least one recording electrode disposed on the distal portion of the MRI- antenna probe member, wherein the MRI-antenna probe member has at least two operational modes, including a first MRI signal operational mode wherein an antenna portion of the MRI-antenna probe member receives MRI signals from local tissue and a second operational recording signal mode wherein the recording electrode obtains electrical signals from local target tissue;
(b) a generally rigid cannula comprising at least two generally concentric tubular members sized and configured to slidably receive the elongate MRI-antenna probe member therein, wherein, in operation, the MRI-antenna probe member cooperates with the cannula to define an internal MRI antenna;
(c) a tuning circuit coupleable to the internal MRI antenna to tune the internal MRI antenna to a MRI frequency;
(d) a RF decoupling circuit configured to isolate the MRI-antenna probe member during an MRI excitation RF transmission; and
(e) a recording splitter circuit to decouple the antenna portion of the MRI-antenna probe member during the recording mode.

15. A kit according to claim 14, wherein the conductor resides substantially in a center of the core of the MRI-antenna probe member.

16. A kit according to claim 14, wherein the core of the MRI-antenna probe member is hollow.

17. A kit according to claim 14, further comprising an implantable flexible elongate stimulation probe sized and configured to slidably extend through an axially extending bore of the cannula.

18. A probe system according to claim 1, wherein the cannula is configured to be inserted into a burr hole placed in a patient's skull, and wherein the recording electrode and the elongate antenna member are configured for deep brain placement.

19. A probe system according to claim 1, wherein the cannula comprises a conductive shielding layer that cooperates with the elongate antenna member to define the MRI receive antenna configured to obtain MRI signals for MRI positional guidance, and wherein, in operation, the elongate antenna member is removed from the cannula and replaced with a stimulation probe which is then inserted to the same location as the elongate antenna member.

20. An in vivo deep brain medical probe system, comprising:
an MRI compatible cannula comprising a plurality of generally concentric axially extending tubes with a receiving bore;
an elongate antenna member with a core comprising a conductor and an insulating layer configured to slidably advance through the cannula bore to cooperate with the cannula to define an MRI receive antenna;
a tuning circuit coupleable to the MRI receive antenna to tune the MRI receive antenna to a MRI frequency,
the elongate antenna member having opposing proximal and distal portions and comprising at least one optic fiber in the core of the antenna member;
the cannula having increased rigidity relative to the antenna member; and the probe system further comprising an RF transmit decoupling circuit in communication with the antenna member, wherein the decoupler circuit is configured to decouple the MRI receive antenna during an MRI RF excitation transmission.

21. A probe system according to claim 20, wherein the core is encased in an MRI compatible conductive material.

22. A probe system according to claim 20, wherein the optic fiber defines the core, and wherein the optic fiber is coated with an MRI compatible conductive material.

23. A probe system according to claim 20, further comprising a fiber optic splitter disposed at a proximal portion of the antenna member that separates the fiber optic core into two light paths, an input path that is adapted to connect to an input light source and an output path that is adapted to connect to a spectrometer.

24. A probe system according to claim 20, wherein the elongate antenna member cooperates with the cannula and provides the MRI receive antenna and an NIR imaging member.

25. A probe system according to claim 20, wherein the core is generally solid.

26. A probe system according to claim 20, wherein the core is generally hollow.

27. A probe system according to claim 20, wherein the plurality of generally concentric axially extending tubes are configured to snugly abut each other.

* * * * *